US008399406B2

(12) United States Patent
Pivetti et al.

(10) Patent No.: US 8,399,406 B2
(45) Date of Patent: Mar. 19, 2013

(54) RECONSTITUTED SURFACTANT COMPOSITION CONTAINING ANALOGS OF SURFACTANT PROTEIN B (SP-B) AND SURFACTANT PROTEIN C (SP-C)

(75) Inventors: Fausto Pivetti, Parma (IT); Monica Bocchi, Parma (IT); Annamaria Soliani Raschini, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 267 days.

(21) Appl. No.: 12/788,480

(22) Filed: May 27, 2010

(65) Prior Publication Data

US 2011/0003733 A1    Jan. 6, 2011

(30) Foreign Application Priority Data

Jun. 5, 2009 (EP) .................................. 09162052

(51) Int. Cl.
*A61K 38/00* (2006.01)
*A61K 38/16* (2006.01)
*A61P 11/00* (2006.01)

(52) U.S. Cl. ........................................ 514/1.5; 514/21.3

(58) Field of Classification Search .................. None
See application file for complete search history.

(56) References Cited

U.S. PATENT DOCUMENTS 7,511,011 B2 * 3/2009 Curstedt et al. ............... 514/1.1
7,842,664 B2 * 11/2010 Curstedt et al. .............. 514/15.5
7,897,577 B2 * 3/2011 Johansson et al. ........... 514/21.3
8,183,210 B2 * 5/2012 Johansson et al. ........... 514/21.3

FOREIGN PATENT DOCUMENTS

WO    2008/044109    4/2008

OTHER PUBLICATIONS

Berge et al. Pharmaceutical Salts. Journal of Pharmaceutical Sciences. Jan. 1977, vol. 66, No. 1, pp. 1-19.*
Bastin et al. Salt Selection and Optimisation Procedures for Pharmaceutical New Chemical Entities. Organic Process Research and Development. 2000, vol. 4, No. 5, pp. 427-435.*
Sweet D G et al., Archives of Disease in Childhood, Education and Practice Edition, vol. 94, No. 3, Jun. 1, 2009 (pp. 78-83).
Palmblad et al., Biochemical Journal, The Biochemical Society, vol. 339, No. 2, Jan. 1, 1999 (pp. 381-386).
Walther F J et al., Molecular Genetics and Metabolism, vol. 71, No. 1/02, Jan. 1, 2000 (pp. 342-351).
Extended European Search Report issued Sep. 25, 2009, in EP 09162052.6 filed Jun. 5, 2009.
F.R. Moya et al., Pediatrics, vol. 115, pp. 1018-1029 (2005).

* cited by examiner

*Primary Examiner* — Marcela M Cordero Garcia
(74) *Attorney, Agent, or Firm* — Oblon, Spivak, McClelland, Maier & Neustadt, L.L.P.

(57) ABSTRACT

Reconstituted pulmonary surfactants comprising a lipid carrier, a combination of polypeptide analog of the native surfactant protein SP-C with a particular polypeptide analog of the native surfactant protein SP-B may be used for the treatment or prophylaxis of RDS and other respiratory disorders.

25 Claims, 2 Drawing Sheets

RECONSTITUTED SURFACTANT COMPOSITION CONTAINING ANALOGS OF SURFACTANT PROTEIN B (SP-B) AND SURFACTANT PROTEIN C (SP-C)

CROSS REFERENCES TO RELATED APPLICATIONS

This application claims priority to European Patent Application No. 09162052.6 filed on Jun. 5, 2009, which is incorporated herein by reference in its entirety.

BACKGROUND OF THE INVENTION

1. Field of the Invention

The present invention relates to reconstituted pulmonary surfactants which are suitable for the prophylaxis and/or treatment of respiratory distress syndrome (RDS) and other respiratory disorders. The present invention also relates to methods for the prophylaxis and/or treatment of respiratory distress syndrome (RDS) and other respiratory disorders by administering such a pulmonary surfactant.

2. Discussion of the Background

The human lung is composed of a large number of small air sacs, called alveoli, in which gases are exchanged between the blood and the air spaces of the lungs. In healthy individuals, this exchange is mediated by the presence of a protein-containing surfactant complex that prevents the lungs from collapsing at the end of expiration.

Lung surfactant complex is composed primarily of lipid and contains minor amounts of various proteins. An absence of adequate levels of this complex results in malfunction of the lung. This syndrome is called Respiratory Distress Syndrome (RDS) and it commonly affects preterm infants.

Said syndrome is effectively treated with commercially available modified natural surfactant preparations extracted from animal lungs, such as the gold standard preparation known as Curosurf®. The main constituents of these surfactant preparations are phospholipids and surfactant hydrophobic proteins B and C (SP-B and SP-C).

Due to the drawbacks of the surfactant preparations from animal tissues, such as the complication of the production process, and possible viral contamination and/or induction of immune reactions, synthetic surfactants have been made available in the art.

Said synthetic surfactants can be simply mixtures of synthetic compounds, primarily phospholipids and other lipids and are known as "artificial" surfactants; although they have been used in clinical practice for many years, their efficacy is not comparable to that of modified natural surfactant.

Artificial surfactants also containing surfactant proteins/peptides are also currently under development. They are termed either "reconstituted" surfactants or "bio-mimetic surfactants".

However, according to the available literature, none of the reconstituted surfactants developed so far has shown an efficacy in terms of lung compliance comparable to that of the surfactants extracted from animals. Moreover they give rise to poor lung gas volumes and grade of alveolar patency at the end of expiration, and a ventilation is required with a positive end expiratory pressure (PEEP) in order to achieve an in vivo activity comparable to that achieved with modified natural surfactants (see, Johansson J et al, J Appl Physiol, 2003, 95, 2055-2063; Davis A J et al, Am J Respir Crit Care Med, 1998; 157, 553-559).

A possible explanation is that the reconstituted surfactants under development do not reproduce the complete proteinaceous profile of the modified natural surfactants as they comprise only one proteinaceous (peptide) component.

On the other hand, besides good efficacy, surfactant compositions should also exhibit a low viscosity to allow the preparation of a concentrated suspension in an aqueous medium. The possibility of preparing a concentrated suspension in a small volume is indeed a feature of particular importance for their administration to very low-weight newborns.

The peptide:phospholipid system is a rather complex mixture whose properties greatly depend on the composition of the phospholipid mixture as well as on the specific phospholipids/peptide combination. The presence of a further peptide would affect the rheological properties of the composition making the system even more complicated.

In the prior art, reconstituted surfactants comprising both SP-B and SP-C analogues resembling human surfactant proteins have been disclosed, for example in WO0076535, WO2008011559 and WO2008044109. However, none of the compositions disclosed therein have been shown to possess optimal properties in terms of lung compliance as well as rheological properties, in particular viscosity.

Accordingly, there is still a need for reconstituted surfactant preparations having a comparable efficacy to that of the surfactants extracted from animal lungs as well as optimal rheological properties allowing their easy delivery and distribution into the broncho-alveolar part of the lungs upon administration.

SUMMARY OF THE INVENTION

Accordingly, it is one object of the present invention to provide novel reconstituted surfactant compositions.

It is another object of the present invention to provide novel reconstituted surfactant compositions with improved properties in terms of lung compliance.

It is another object of the present invention to provide novel reconstituted surfactant compositions with improved properties in terms of viscosity.

It is another object of the present invention to provide novel reconstituted surfactant compositions with improved properties in terms of lung compliance and viscosity.

It is another object of the present invention to provide novel methods for the prophylaxis and/or treatment of respiratory distress syndrome (RDS) and other respiratory disorders by administering such a pulmonary surfactant composition.

These and other objects, which will become apparent during the following detailed description, have been achieved by the inventors' discovery that of reconstituted surfactant compositions with improved properties in terms of lung compliance and viscosity.

Thus, in a first embodiment, the present invention provides a reconstituted surfactant comprising:

(a) 1.2 to 1.8% by weight of a polypeptide analog of the native surfactant protein SP-C having the sequence represented by the formula:

IPSSPVHLKRLKLLLLLLLLILLLILGALLLGL; (SEQ. ID NO: 1)

(b) 0.1 to 0.5% by weight of a polypeptide analog of the native surfactant protein SP-B having the sequence represented by the formula:

(SEQ. ID NO: 2)
CWLCRALIKRIQALIPKGGRLLPQLVCRLVLRCS;
and (c) a monounsaturated and a saturated phospholipid in a weight ratio of 45:55 to 55:45;

all of the amounts being calculated relative to the total weight of (a), (b), and (c).

The present invention also provides pharmaceutical compositions comprising the claimed reconstituted surfactant alone or in combination with one or more pharmaceutically acceptable carriers.

The present invention also provides the use of the claimed reconstituted surfactant as a medicament.

In a further aspect, the present invention provides the use of the claimed reconstituted surfactant for the prophylaxis and/or treatment of respiratory distress syndrome (RDS) and other respiratory disorders.

Moreover, the present invention provides the use of the claimed reconstituted surfactant for the manufacture of a medicament for the prophylaxis and/or treatment of respiratory distress syndrome (RDS) and other respiratory disorders.

The present invention also provides a method for the prophylaxis and/or treatment of respiratory distress syndrome (RDS) and other respiratory disorders, said method comprising administering to a patient in need of such treatment a therapeutically effective amount of the reconstituted surfactant mentioned above.

In a further embodiment, the present invention provides a method comprising administering the dilute reconstituted surfactant of the invention to the lung by a lavage technique to remove injurious material and/or inflammatory exudate, to expand the lung and to improve pulmonary function.

The present invention also provides a kit, comprising:

(a) the aforementioned reconstituted surfactant in powder form in a first unit dosage form;

(b) a pharmaceutically acceptable carrier in a second unit dosage form; and (c) a container which contains the first and second dosage forms.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
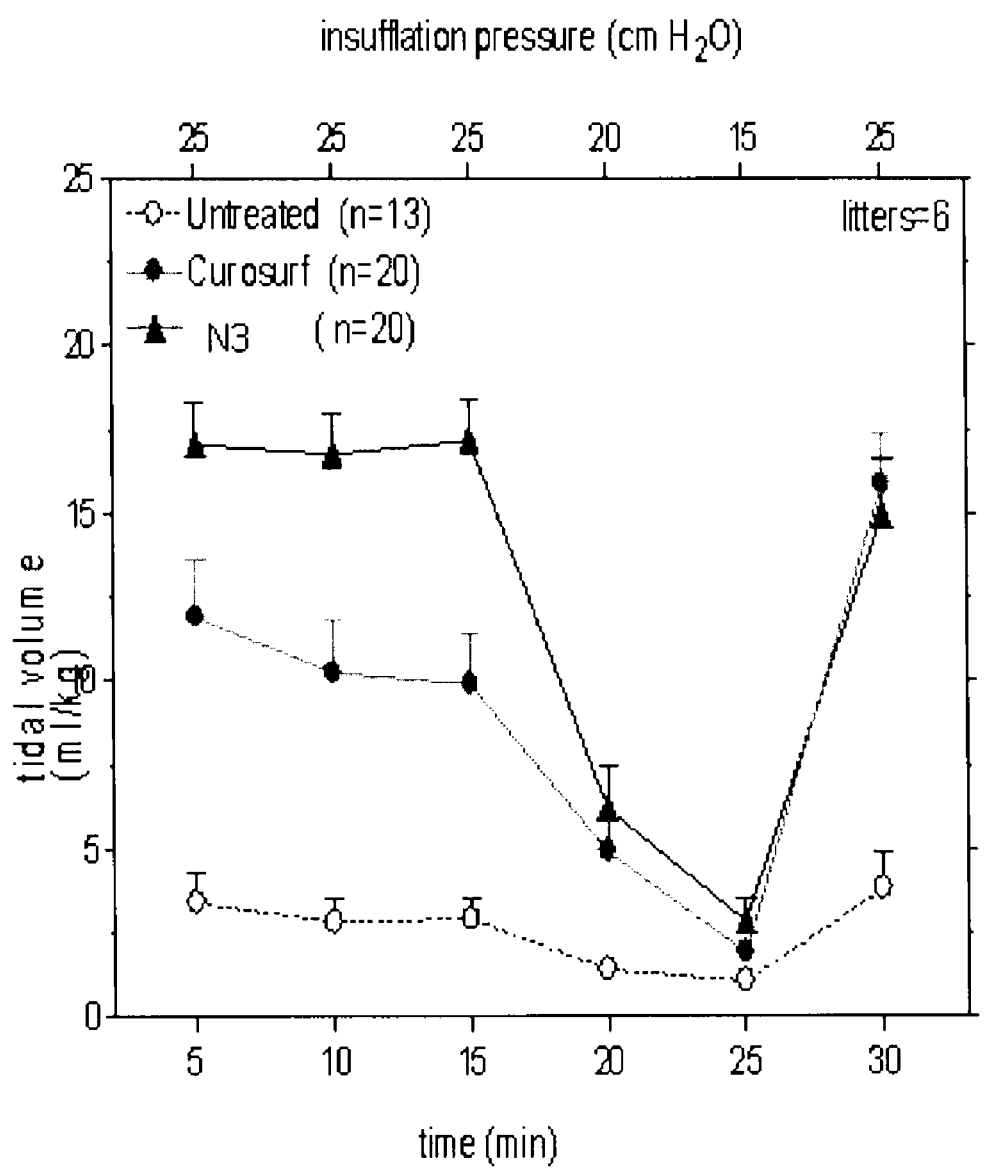
FIG. 1 shows the results in terms of tidal volumes (ml/kg) as a function of time/pressure of a reconstituted surfactant of the invention (N3) versus Curosurf® and untreated animals (n=number of animals).

"Surfactant activity" for a surfactant preparation is defined as the ability to lower the surface tension.

The in vitro efficacy of exogenous surfactant preparations is commonly tested by measuring its capability of lowering the surface tension using suitable apparatus such as Wilhelmy Balance and Captive Bubble Surfactometer.

The in vivo efficacy of exogenous surfactant preparations is commonly tested by measuring two parameters:

i) the tidal volume which is an index of the lung compliance; and ii) the lung gas volume which is an index of the alveolar air expansion or patency at the end of expiration, and hence of the capability of forming a stable phospholipid film in the alveoli at the end of expiration.

A "Therapeutically effective" amount as used herein refers to an amount of reconstituted surfactant capable of preventing, avoiding, reducing or eliminating the respiratory disease or disorders associated with the lack or dysfunction of endogenous surfactant.

The term "pharmaceutically acceptable" or "physiologically tolerable" refers to compositions, medium, solvents, salts capable of being administered to a human without the production of undesirable physiological effects.

The term "polypeptide analog of the native surfactant protein SP-C", means a polypeptide having an amino acid sequence in which, compared to the native SP-C protein, amino acids are missing and/or have been replaced by other amino acids, so long as the polypeptide, in a mixture with phospholipids, show pulmonary surfactant activity (as demonstrable by in vitro and in vivo efficacy assays).

The term "polypeptide analog of the native surfactant protein SP-B", means a polypeptide having an amino acid sequence in which, compared to the native SP-B protein, amino acids are missing and/or have been replaced by other amino acids so long as the polypeptide, in a mixture with phospholipids, show pulmonary surfactant activity (as demonstrable by in vitro and in vivo efficacy assays).

"Recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein.

As used herein, the term "about" applied to a point value, indicates a variability of ±1%.

Phospholipids are lipids in which one fatty acid has been replaced by a phosphate group and a simple organic molecule. The most common class of phospholipids which can be found in surfactant preparations are: phosphatidylcholines (PC), phosphatidylethanolamine (PE) phosphatidylglycerol (PG), phosphatidylinositol (PI), and phosphatidylserine (PS).

The glycerol moieties of the phospholipids are mainly esterified with long chain fatty acids which in turn can be saturated (e.g. myristic, palmitic, and stearic acid), monounsaturated (e.g. oleic acid) or polyunsaturated (e.g. linoleic and arachidonic acid).

In particular, the species taken into consideration in the application are:

1,2-dipalmitoyl-sn-glycero-3-phosphocholine, also known as dipalmitoyl-phosphatidylcholine (DPPC), which is a saturated derivative; and 1-palmitoyl-2-oleyl-sn-glycero-3-phosphoglycerol, also known as palmitoyl-oleyl-phosphatidylglycerol (POPG) which is a monounsaturated derivative.

"Polypeptide", "peptide" and "protein" are used interchangeably herein to refer to a polymer of amino acid residues.

The amino acid sequences are shown according to the one-letter code with the amino acid which carries the free amino group at the left end (amino terminus) and the amino acid which carries the free carboxyl group at the right end (carboxy terminus).

All the amino acid residues identified herein are in the natural L-configuration and the sequences identified herein are reported according to standard abbreviations for amino acid residues. For avoidance of doubt, the amino acid derivative L-nor-leucine is referred to herein as nLeu, and L-ornithine is abbreviated as Orn.

A multi-factor experimental design was built-up to investigate how the viscosity is affected by the relative amounts of the phospholipids and the SP-B and SP-C analogues in the surfactant compositions generically disclosed in WO 2008/044109, as well as how said components are influenced by each other in reconstituted surfactants.

It has been found that the amount of SP-B analog has a significant effect on the viscosity of the surfactant composition, and hence that the content of the SP-B analog should be maintained as low as possible compatible with a therapeutic efficacy in order to reduce the viscosity of the reconstituted surfactant to acceptably low levels.

WO 2008/044109 is directed to the use of DPPC:POPG ratios preferably equal to or higher than 7:3, in the presence of an SP-B analog. WO 2008/044109 is silent on the viscosity of such surfactant compositions. It has now been found that when the SP-B analog amount in the surfactant is minimized high ratios between disaturated phospholipids such as DPPC and unsaturated phospholipids such as POPG leads to an unacceptably high viscosity of the corresponding composition. However, we have overcome this problem by preparing low SP-B surfactants in which the ratio of unsaturated phospholipid to saturated phospholipid is reduced below the ratios disclosed in the prior art, preferably to about 1:1, and have shown that these surfactant compositions have a surprisingly low viscosity, which renders them useful for all clinical applications.

Thus, in one embodiment the present invention provides a reconstituted surfactant comprising:

(a) 1.2 to 1.8% by weight of a polypeptide analog of the native surfactant protein SP-C having the sequence represented by the formula:

(SEQ. ID NO: 1)
IPSSPVHLKRLKLLLLLLLLILLLILGALLLGL;

(b) 0.1 to 0.5% by weight of a polypeptide analog of the native surfactant protein SP-B having the sequence represented by the formula:

(SEQ. ID NO: 2)
CWLCRALIKRIQALIPKGGRLLPQLVCRLVLRCS;
and (c) a monounsaturated and a saturated phospholipid in a weight ratio of 45:55 to 55:45;

all the amounts being calculated relative to the total weight of (a), (b), and (c).

In the reconstituted surfactant of the invention the SP-C protein analog component is preferably present in an amount of 1.4 and 1.6%, and more preferably about 1.5% by weight, based on the total weight of the reconstituted surfactant.

In the reconstituted surfactants of the invention the SP-B protein analog component is preferably present in an amount of 0.2 and 0.4%, more preferably about 0.2% by weight, based on the total weight of the reconstituted surfactant The reconstituted surfactant of the invention may advantageously comprise saturated phospholipids such as dipalmitoylphosphatidylcholine (DPPC) and dipalmitoylphosphatidylglycerol (DPPG) and monounsaturated phospholipids such as palmitoyloleoylphosphatidylcholine (POPC) and palmitoyloleoylphosphatidylglycerol (POPG).

The preferred saturated phospholipid for use according to the invention is DPPC, while the preferred monounsaturated phospholipid is POPG.

Advantageously, the combined weight of the phospholipids comprises at least 90%, advantageously at least 95%, preferably at least 97.7%, more preferably 98.3% of the total weight of the reconstituted surfactant.

In one embodiment, the present invention provides a reconstituted surfactant comprising:

(a') about 1.5% by weight of a polypeptide analog of the native surfactant protein SP-C having the sequence represented by the formula:

(SEQ. ID NO: 1)
IPSSPVHLKRLKLLLLLLLLILLLILGALLLGL;

(b') about 0.2% by weight of a polypeptide analog of the native surfactant protein SP-B having the sequence represented by the formula:

(SEQ. ID NO: 2)
CWLCRALIKRIQALIPKGGRLLPQLVCRLVLRCS;
and (c') 1,2-dipalmitoyl-sn-glycero-3-phosphocholine (DPPC) and 1-palmitoyl-2-oleyl-sn-glycero-3-phosphoglycerol (POPG) in a weight ratio of about 50:50 all the amounts being calculated relative to the total weight of (a'), (b'), and (c').

In one specific embodiment, the present invention provides to a reconstituted surfactant composition comprising:

(a") about 1.5% by weight of a polypeptide analog of the native surfactant protein SP-C having the sequence represented by the formula:

(SEQ. ID: NO. 1)
IPSSPVHLKRLKLLLLLLLLILLLILGALLLGL;

(b") about 0.2% by weight of a polypeptide analog of the native surfactant protein SP-B having the sequence represented by the formula:

(SEQ. ID: NO. 2)
CWLCRALIKRIQALIPKGGRLLPQLVCRLVLRCS;

(c") about 49.15% by weight of 1,2-dipalmitoyl-sn-glycero-3-phosphocholine (DPPC); and (d") about 49.15% by weight of 1-palmitoyl-2-oleyl-sn-glycero-3-phosphoglycerol (POPG);

all the amounts being calculated on the total weight of (a"), (b"), (c") and (d").

In a preferred embodiment, the polypeptide of SEQ ID:NO.2 may be in the form of disulfide linked molecule wherein the intramolecular disulfide linkages are between the two cysteine residues at the 1- and 33-positions and/or between the two cysteine residues at the 4- and 27-positions.

The polypeptide of SEQ ID:NO. 1 has been referred to in WO 2008/044109 (incorporated herein in its totality by reference) as SP-C33(Leu), while the polypeptide of SEQ ID:2 has been referred to in WO 2008/044109 to as Mini-B(Leu), and its disulfide linked form as ox Mini-B(Leu).

In even more preferred embodiments, the reconstituted surfactant of the invention consists essentially of the components (a), (b), and (c) or the components (a'), (b'), and (c') or the components (a"), (b"), (c"), and (d") in the claimed amounts.

Advantageously both polypeptides may be present in the form of pharmaceutically acceptable salts. Said salts include for example, salts of hydrochloric acid, acetic acid, and trifluoroacetic acid.

Preferably both polypeptides are present in the composition in the form of acetates.

Also POPG may advantageously be present in the form of pharmaceutically acceptable salts, for example as sodium salt (POPG Na).

The polypeptides of SEQ ID:NO.1 and SEQ ID:NO.2 may be prepared according to synthetic methods or recombinant techniques well known to persons skilled in the art. An excellent summary of the many techniques available may be found in J. M. Steward and J. D. Young, "Solid Phase Peptide Synthesis", W.H. Freeman Co., San Francisco, 1969, and J. Meienhofer, Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis.

The polypeptides may preferably be prepared using the solid-phase synthetic technique initially described by Merrifield, in J. Am. Chem. Soc. 85: 2149-2154 (1963). Other polypeptide synthesis techniques may be found, for example, in M. Bodanszky et al., Peptide Synthesis, John Wiley & Sons, 2d Ed., (1976) as well as in other reference works known to those skilled in the art.

Appropriate protective groups for use in such syntheses will be found in the above texts as well as in J. F. W. McOmie, Protective Groups in Organic Chemistry, Plenum Press, New York, N.Y. (1973).

For example, both polypeptides may be prepared as described in WO2008/044109.

Effective doses of the reconstituted surfactant of the invention for the treatment of a disease such as RDS, as described herein, vary depending upon many different factors, including type of the disease, means of administration, weight and physiological state of the patient, and whether treatment is prophylactic or therapeutic.

In general, the dose is comprised from 0.01 mg to 10 g per kg of body weight, preferably from 0.1 to 1 g per kg of body weight, and the frequency of administration can vary depending on whether the treatment is prophylactic or therapeutic. Typically a dose of about 50 mg/kg, 100 mg/kg, or 200 mg/kg is administered in one dose. For use in newborns, one or two administrations are generally sufficient.

Although needs can vary depending on the severity of the respiratory disease and/or other variables, the determination of the optimal ranges for effective dosages is within the skill of the skilled person in the art.

The present invention also provides pharmaceutical formulations comprising the reconstituted surfactant of the invention.

Said formulations are advantageously administered in the form of a solution, dispersion, suspension or dry powder. Preferably said compositions comprise the reconstituted surfactant dissolved or suspended in a suitable physiologically tolerable solvent or re-suspension carrier, such as water or a physiological saline aqueous solution (about 0.9% w/v NaCl).

The formulations of the present invention may comprise aqueous solutions, preferably sterile, which may also comprise pH buffering agents, diluents and other suitable additives.

The formulations may be presented in unit-dose or multi-dose containers, for example sealed ampoules and vials, or may be stored in a frozen or freeze-dried (lyophilized) condition requiring only the addition of sterile liquid carrier immediately prior to use.

Preferably, the reconstituted surfactant of the invention is supplied as sterile suspension in a buffered physiological saline aqueous solution in single-use glass vials.

The pharmaceutical formulations may be prepared according to conventional techniques well known in the pharmaceutical industry. Such techniques include the step of admixing the polypeptides and the phospholipids in the presence of an organic solvent. The solvent is then removed by dialysis or evaporation under nitrogen and/or exposure to vacuum or by other appropriate techniques well known to the skilled person in the art, such as lyophilisation.

Advantageously, the amount of residual solvents may be less than 0.1%, preferably less than 0.05%, more preferably less than 0.003%, even more preferably less than 0.001% by weight.

The obtained powder is then uniformly and intimately brought into association with liquid carriers or finely divided solid carriers or both.

The mixture of polypeptides and phospholipids can be sterilized before removing the solvent for example by sterile filtration. In certain other embodiments, the reconstituted surfactant composition is terminally sterilized according to methods well known in the art.

The administration of the reconstituted surfactant of the invention is carried out in a manner known to the person skilled in the art, e.g. by intratracheal installation (infusion or bolus or through a catheter), by spray administration, or nebulisation.

As disclosed herein, the invention contemplates the use of both concentrated and dilute surfactant formulations, depending upon the particular use, as described further herein. Concentrated surfactant compositions are typically used for "bolus" type administrations, whereas dilute surfactant compositions are typically used for "lavage" type administrations.

Advantageously the viscosity of said formulations is less than 20 cP, preferably less than 15 cP, upon determination with a common viscometer available on the market according to methods well know in the art.

Advantageously, for "bolus" type administration, the reconstituted surfactant concentration in terms of weight per ml of solution or suspension (following addition of a liquid carrier) is in the range of from about 0.1 to about 100 mg/ml, preferably between 5 and 80 mg/ml.

In a preferred embodiment of the invention, when the reconstituted surfactant is administered by intratracheal instillation as a suspension in physiological saline (about 0.9% w/v sodium chloride in water), the concentration is about 80 mg/ml.

Therefore, a preferred embodiment of the invention concerns a pharmaceutical formulation in form of aqueous suspension in physiological saline comprising about 80 mg/ml of a reconstituted surfactant comprising:

(a") about 1.5% by weight of a polypeptide analog of the native surfactant protein SP-C having the sequence represented by the formula:

(SEQ ID: NO. 1)
IPSSPVHLKRLKLLLLLLLLILLLILGALLLGL;

(b") about 0.2% by weight of a polypeptide analog of the native surfactant protein SP-B having the sequence represented by the formula:

(SEQ ID: NO. 2)
CWLCRALIKRIQALIPKGGRLLPQLVCRLVLRCS;

(c") about 49.15% by weight of 1,2-dipalmitoyl-sn-glycero-3-phosphocholine (DPPC); and (d") about 49.15% by weight of 1-palmitoyl-2-oleyl-sn-glycero-3-phosphoglycerol (POPG);

all the amounts being calculated on the total weight of (a"), (b"), (c") and (d").

Typically the viscosity of said formulation is about 9±3 cP at 25° C. and 8±3 cP at 37° C. as determined using a common rotational viscosimeter available on the market.

When used for lavage administration, a typical surfactant concentration of from about 0.1 to 20 mg/ml, and more preferably about 0.5 to 10 mg/ml (in terms of mg surfactant per ml of solution or suspension).

Since it depends on the concentration, the viscosity of diluted formulations would be even lower.

When used as a pharmaceutical treatment, the formulations comprising the reconstituted surfactant of the present invention may be administered either alone or optionally in conjunction with other compounds or compositions that are used in the treatment of respiratory diseases or disorders. For example, if a subject is being treated for a respiratory disorder caused by a bacterial infection, then the reconstituted surfactant of the present invention may be administered in conjunction with another compound used to treat the bacterial infection, such as an antibiotic.

Otherwise, in certain cases, for example for preventing complications such as bronchopulmonary dysplasia, the reconstituted surfactant of the present invention may be administered in conjunction with a corticosteroid such as budesonide and/or beclometasone dipropionate.

In certain embodiments, the reconstituted surfactant of the invention, and the re-suspension carrier may be separately packed at the same time in a suitable container. Such separate packaging of the components in a suitable container is also described as a kit.

Therefore, this invention is also directed to a kit, comprising:
(a) a reconstituted surfactant of the invention in a powder form in a first unit dosage form;
(b) a pharmaceutically acceptable carrier in a second unit dosage form; and
(c) a container which contains said first and second dosage forms.

Preferably the pharmaceutically acceptable carrier is a physiological saline aqueous solution, more preferably sterile.

The container may be any suitable container such as a cardboard box or a foil pouch.

As disclosed herein, a variety of methods for administering the reconstituted surfactant and formulations thereof of the present invention are available and are well known by one of skill in the art.

Depending on the type of disease e.g., an infant or adult with respiratory distress syndrome, different treatment methods can be appropriate.

Typically the surfactant is administered by endotracheal instillation to patients (e.g. pre-term infants) kept under continuous or intermittent positive pressure ventilation (IPPV).

Alternatively, the surfactant may be administered by the use of a thin catheter placed in the trachea and the patient respiration supported through specially designed nasal devices such as masks, prongs or tubes according to methodology known as nasal Continuous Positive Airway Pressure (nCPAP).

The latter approach would be only possible with a surfactant having a low viscosity, as a high viscosity would make the passage of the surfactant through the thin catheter more difficult.

In instances in which the patient suffers from a respiratory distress condition associated with pulmonary inflammation, pulmonary infection or pulmonary contusion, particular treatment modalities can be recommended. In one such therapeutic method, lavage of the patient's lungs with a surfactant composition of the present invention is performed as a single or multiple treatments.

The reconstituted surfactant of the invention is suitable to prevent, delay, alleviate, arrest, or inhibit development of the symptoms or conditions associated with a respiratory disease.

In particular, it is useful for the prophylaxis and/or treatment of respiratory distress syndrome (RDS) in prematurely born babies or other diseases related to a surfactant-deficiency or dysfunction including acute lung injury (ALI), RDS in adults (ARDS), meconium aspiration syndrome (MAS), and bronchopulmonary dysplasia (BPD).

It may also be useful for the prophylaxis and/or treatment of other respiratory disorders such as chronic obstructive pulmonary disease (COPD), asthma, respiratory infection (e.g. pneumonia, pneumocystits carinii, cystic fibrosis and respiratory syncitial virus) as well as for the treatment of serous otitis media (glue ear).

Other features of the invention will become apparent in the course of the following descriptions of exemplary embodiments which are given for illustration of the invention and are not intended to be limiting thereof.

EXAMPLES

Example 1

Influence of the Components on the Viscosity

A multi-factor experimental design is constructed to evaluate the influence of components on the formulation in terms of viscosity. Different percentages of the polypeptides SP-C33 (leu) and ox-Mini-B(leu) as well as different ratios of DPPC and POPG Na are tested.

All the obtained mixtures are re-suspended in physiological saline aqueous solution (0.9% w/v) at a concentration of 80 mg/ml.

The viscosity is determined at 25° C. and 37° C. using a VISCO STAR Plus (Fungilab) viscometer applying a rotation speed of 100 r.p.m.

For sake of comparison, Curosurf® exhibits a viscosity comprised between 6 and 10 mPas (1 mPas=1 centipoise). The results are reported in Table 1.

TABLE 1

| Composition | N1 | N2 | N3 | N4 | N5 | N6 | N8 | N9 |
|---|---|---|---|---|---|---|---|---|
| % SPC33(leu) | 0.5% | 0.5% | 1.5% | 1.5% | 1% | 1.5% | 1.5% | 0.5% |
| % ox-MiniB(leu) | 0.2% | 1% | 0.2% | 1% | 0.5% | 0.2% | 1% | 1% |
| DPPC/POPG Na | 3 | 1 | 1 | 3 | 2 | 3 | 1 | 3 |
| Viscosity 25° C. (cP) | 54.3 | 288 | 9.7 | 56.8 | 83.4 | 554.9 | 671.2 | 73.8 |
| Viscosity 37° C. (cP) | 29.8 | 700 | 7.2 | 37.1 | 33.7 | 119.8 | 338.1 | 37.0 |

The results indicate that at low concentrations of ox-Mini-B(leu) and in the presence of a low ratio between DPPC and POPG (column N3 in Table 1) the viscosity of the mixture is also very low. These results suggest that by minimizing the amount of SP-B analog in the surfactant and simultaneously reducing the concentration of saturated phospholipid relative to unsaturated phospholipid a composition is obtainable with a viscosity that is low enough to be used for all surfactant applications, including use in concentrated form.

Example 2

Characterization of the Reconstituted Surfactant N3

A mixture of DPPC:POPG Na in a 1:1 ratio, SPC-33(leu) and ox Mini-B(leu) in the percentage amounts reported for the composition N3 in Table 1 of Example 1 is dissolved in chloroform/ethanol 98:2 (v/v).

The solvent is evaporated and the resulting powder is subsequently hydrated in 0.9% w/v NaCl aqueous solution under stirring, to give a surfactant concentration of 80 mg/ml. The unitary composition is reported in Table 2.

TABLE 2

| Ingredient | % | Conc |
|---|---|---|
| SP-C33(leu) | 1.5 | 1.2 mg/ml |
| Ox-Mini-B(leu) | 0.2 | 0.16 mg/ml |
| DPPC | 49.15 | 39.32 mg/ml |
| POPG Na | 49.15 | 39.32 mg/ml |

The viscosity of said formulation is confirmed to be very low, e.g about 9 cP at 25° C. and about 7 cP at 37° C. Moreover it does not change after 6 months of storage at 5° C.

The formulation turns also out to be chemically stable after 6 months of storage and the overall amount of phospholipids lysoforms detected by HPLC is less than 1% by weight.

Example 3

In Vivo Activity of the Reconstituted Surfactant N3

The reconstituted surfactant of Example 2 is assayed in premature newborn rabbits, obtained by hysterectomy at the gestational age of 27 days. The experiments are performed without applying a positive end expiratory pressure (PEEP).

Animals receiving Curosurf® serve as positive controls and non-treated littermates as negative controls.

All surfactant preparations are administered at a concentration of 80 mg/ml and at a standard dose of 2.5 ml/kg.

The immature newborn rabbits are ventilated in parallel with a standardized sequence of peak insufflation pressures. To open up the lungs, pressure is first set at 35 cmH$_2$O for 1 minute. After this recruitment manoeuvre, pressure is lowered to 25 cmH$_2$O for 15 minutes and further on to 20 and 15 cm H$_2$O. Finally, pressure is raised again to 25 cmH$_2$O for 5 minutes, after which the lungs are ventilated for additional 5 minutes with nitrogen and then excised for gas volume measurements.

Figure 2:
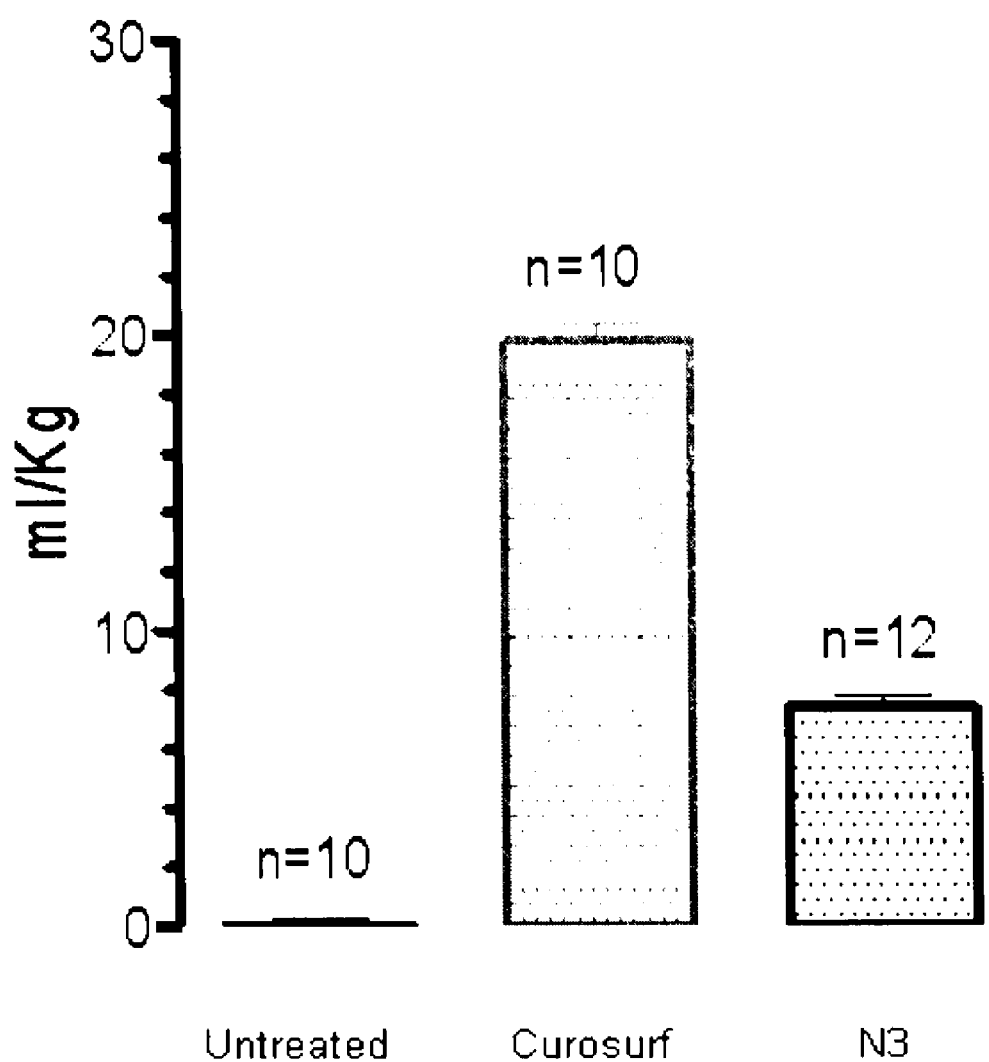
FIG. 2 shows the results in terms of lung gas volumes (ml/kg) of a reconstituted surfactant of the invention (N3) versus Curosurf® and untreated animals (n=number of animals).

Both tidal volumes and lung gas volumes, expressed as ml/kg, are measured and the results, given as median values, are reported in FIGS. 1 and 2, respectively. From FIG. 1 it can be appreciated that animals treated with the reconstituted surfactant of the invention show an improvement of the tidal volumes slightly better than that achieved after administration of Curosurf®. This result suggests that the reconstituted artificial surfactant of the invention may deliver better clinical efficacy than the current gold standard in the field.

As far as the lung gas volumes are concerned, FIG. 2 demonstrates that the reconstituted surfactant of the invention is capable of giving rise to a value comparable with that of reconstituted surfactant tested in Example 3 of WO 2008/044109 which contains a higher ratio between DPPC and POPG (68:31). Moreover the lung gas volumes value of the reconstituted surfactant of the invention turns out to be robust and reproducible.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A reconstituted surfactant composition, comprising:
   (a) 1.2 to 1.8% by weight of a polypeptide analog of the native surfactant protein SP-C having the sequence represented by the formula:

IPSSPVHLKRLKLLLLLLLLILLLILGALLLGL; (SEQ. ID NO: 1)

or a pharmaceutically acceptable salt thereof;
   (b) 0.1 to 0.5% by weight of a polypeptide analog of the native surfactant protein SP-B having the sequence represented by the formula:

CWLCRALIKRIQALIPKGGRLLPQLVCRLVLRCS; (SEQ. ID NO: 2)
   and or a pharmaceutically acceptable salt thereof; and
   (c) a monounsaturated and a saturated phospholipid in a weight ratio of 45:55 to 55:45;
   all the amounts being calculated relative to the total weight of (a), (b), and (c),
   wherein the C residues at positions 1 and 33 of SEQ. ID NO:2 may be linked by a disulfide bond and the C residues at positions 4 and 27 of SEQ. ID NO:2 may be linked by a disulfide bond.

2. A reconstituted surfactant, comprising:
   (a') about 1.5% by weight of a polypeptide analog of the native surfactant protein SP-C having the sequence represented by the formula:

IPSSPVHLKRLKLLLLLLLLILLLILGALLLGL; (SEQ. ID NO: 1)

or a pharmaceutically acceptable salt thereof;
   (b') about 0.2% by weight of a polypeptide analog of the native surfactant protein SP-B having the sequence represented by the formula:

CWLCRALIKRIQALIPKGGRLLPQLVCRLVLRCS; (SEQ. ID NO: 2)
   and or a pharmaceutically acceptable salt thereof; and
   (c') 1,2-dipalmitoyl-sn-glycero-3-phosphocholine (DPPC) and 1-palmitoyl-2-oleyl-sn-glycero-3-phosphoglycerol (POPG) or a pharmaceutically acceptable salt of POPG in a weight ratio of about 50:50 all the amounts being calculated relative to the total weight of (a'), (b'), and (c'),
   wherein the C residues at positions 1 and 33 of SEQ. ID NO:2 may be linked by a disulfide bond and the C residues at positions 4 and 27 of SEQ. ID NO:2 may be linked by a disulfide bond.

3. A reconstituted surfactant according to claim 2, comprising:
   (a") about 1.5% by weight of a polypeptide analog of the native surfactant protein SP-C having the sequence represented by the formula:

IPSSPVHLKRLKLLLLLLLLILLLILGALLLGL; (SEQ ID: NO. 1)

or a pharmaceutically acceptable salt thereof;
   (b") about 0.2% by weight of a polypeptide analog of the native surfactant protein SP-B having the sequence represented by the formula:

CWLCRALIKRIQALIPKGGRLLPQLVCRLVLRCS; (SEQ ID: NO. 2)

or a pharmaceutically acceptable salt thereof;
   (c") about 49.15% by weight of 1,2-dipalmitoyl-sn-glycero-3-phosphocholine (DPPC); and
   (d") about 49.15% by weight of 1-palmitoyl-2-oleyl-sn-glycero-3-phosphoglycerol (POPG) or a pharmaceutically acceptable salt of POPG;
   all the amounts being calculated on the total weight of (a"), (b"), (c") and (d").
   wherein the C residues at positions 1 and 33 of SEQ. ID NO:2 may be linked by a disulfide bond and the C residues at positions 4 and 27 of SEQ. ID NO:2 may be linked by a disulfide bond.

4. A reconstituted surfactant according to claim 1, wherein said polypeptide of SEQ ID:NO.2 is in the form of disulfide linked molecule with the intramolecular disulfide linkage between the two cysteine residues at the 1- and 33-positions and/or between the two cysteine residues at the 4- and 27-positions.

5. A reconstituted surfactant according to claim 2, wherein the polypeptide of SEQ ID:NO.2 is in the form of disulfide linked molecule with the intramolecular disulfide linkage between the two cysteine residues at the 1- and 33-positions and/or between the two cysteine residues at the 4- and 27-positions.

6. A reconstituted surfactant according to claim 3, wherein the polypeptide of SEQ ID:NO.2 is in the form of disulfide linked molecule with the intramolecular disulfide linkage between the two cysteine residues at the 1- and 33-positions and/or between the two cysteine residues at the 4- and 27-positions.

7. A reconstituted surfactant according to claim 2, wherein said POPG is in the form of a pharmaceutically acceptable salt.

8. A reconstituted surfactant according to claim 3, wherein said POPG is in the form of a pharmaceutically acceptable salt.

9. A reconstituted surfactant according to claim 7, wherein the salt is the sodium salt.

10. A reconstituted surfactant according to claim 8, wherein the salt is the sodium salt.

11. A reconstituted surfactant according to claim 1, wherein each of said polypeptides is present in the form of a pharmaceutically acceptable salt.

12. A reconstituted surfactant according to claim 2, wherein each of said polypeptides is present in the form of a pharmaceutically acceptable salt.

13. A reconstituted surfactant according to claim 3, wherein each of said polypeptides is present in the form of a pharmaceutically acceptable salt.

14. A reconstituted surfactant according to 11, wherein the salt is the acetate salt.

15. A reconstituted surfactant according to 12, wherein the salt is the acetate salt.

16. A reconstituted surfactant according to 13, wherein the salt is the acetate salt.

17. A pharmaceutical formulation comprising a reconstituted surfactant according to claim 1, said formulation being in the form of a solution, a dispersion, a suspension or a dry powder, optionally in combination with one or more pharmaceutically acceptable carriers.

18. A pharmaceutical formulation according to claim 17, wherein said formulation is in the form of an aqueous suspension.

19. A pharmaceutical formulation according to claim 18, wherein said reconstituted surfactant is present in a concentration of 0.1 to 160 mg/ml of the aqueous suspension.

20. A kit, comprising:
(a) a reconstituted surfactant according to claim 1 in powder form in a first unit dosage form;
(b) a pharmaceutically acceptable carrier in a second unit dosage form; and
(c) a container which contains said first and second dosage forms.

21. A method for the treatment or prophylaxis of respiratory distress syndrome (RDS) in prematurely born babies or for the treatment or prophylaxis of other diseases related to a surfactant-deficiency or dysfunction, said method comprising administering to a subject in need thereof an effective amount of a reconstituted surfactant according to claim 1.

22. A method according to claim 21, wherein said disease is RDS in and adult (ARDS), meconium aspiration syndrome (MAS), or bronchopulmonary dysplasia (BPD).

23. A reconstituted surfactant according to claim 1, wherein said polypeptide of SEQ ID:NO.2 is in the form of disulfide linked molecule with intramolecular disulfide linkages between the two cysteine residues at the 1- and 33-positions and between the two cysteine residues at the 4- and 27-positions.

24. A reconstituted surfactant according to claim 2, wherein the polypeptide of SEQ ID NO:2 is in the form of disulfide linked molecule with intramolecular disulfide linkages between the two cysteine residues at the 1- and 33-positions and between the two cysteine residues at the 4- and 27-positions.

25. A reconstituted surfactant according to claim 3, wherein the polypeptide of SEQ ID NO:2 is in the form of disulfide linked molecule with intramolecular disulfide linkages between the two cysteine residues at the 1- and 33-positions and between the two cysteine residues at the 4- and 27-positions.

* * * * *

SEQUENCE LISTING

```
<160> NUMBER OF SEQ ID NOS: 2

<210> SEQ ID NO 1
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ile Pro Ser Ser Pro Val His Leu Lys Arg Leu Lys Leu Leu Leu Leu
1               5                   10                  15

Leu Leu Leu Leu Ile Leu Leu Leu Ile Leu Gly Ala Leu Leu Leu Gly
            20                  25                  30

Leu
```

```
<210> SEQ ID NO 2
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Cys Trp Leu Cys Arg Ala Leu Ile Lys Arg Ile Gln Ala Leu Ile Pro
1               5                   10                  15

Lys Gly Gly Arg Leu Leu Pro Gln Leu Val Cys Arg Leu Val Leu Arg
            20                  25                  30

Cys Ser
```